United States Patent [19]

Bronowicki

[11] Patent Number: 5,656,779
[45] Date of Patent: Aug. 12, 1997

[54] APPARATUS AND METHOD FOR PRODUCING STRUCTURAL AND ACOUSTIC VIBRATIONS

[75] Inventor: Allen J. Bronowicki, Laguna Niguel, Calif.

[73] Assignee: TRW Inc., Redondo Beach, Calif.

[21] Appl. No.: 378,437

[22] Filed: Jan. 26, 1995

Related U.S. Application Data

[63] Continuation-in-part of Ser. No. 986,035, Dec. 4, 1992, Pat. No. 5,351,527, and a continuation-in-part of Ser. No. 311,607, Sep. 23, 1994.

[51] Int. Cl.$^6$ .............................. G01N 29/00; H04R 9/04; B06B 3/00
[52] U.S. Cl. .................. 73/668; 73/663; 73/703
[58] Field of Search .................. 73/579, 662, 663, 73/668, 702, 703; 318/128

[56] References Cited

U.S. PATENT DOCUMENTS

| | | |
|---|---|---|
| 3,027,747 | 4/1962 | York et al. ............... 73/668 |
| 3,290,922 | 12/1966 | Thompson . |
| 3,435,664 | 4/1969 | Harris . |
| 3,438,493 | 4/1969 | Goble . |
| 3,608,715 | 9/1971 | Snyder et al. . |
| 3,691,521 | 9/1972 | Schaefer . |
| 3,745,384 | 7/1973 | Blanchard . |
| 3,771,121 | 11/1973 | Lohr . |
| 3,774,150 | 11/1973 | Matsui et al. . |
| 3,781,788 | 12/1973 | Schiester et al. . |
| 3,802,252 | 4/1974 | Hayward et al. . |
| 3,810,655 | 5/1974 | Pracher . |
| 3,942,381 | 3/1976 | Brown et al. . |
| 4,049,935 | 9/1977 | Gruber . |
| 4,062,227 | 12/1977 | Heyman . |
| 4,187,718 | 2/1980 | Schibasaki . |
| 4,197,564 | 4/1980 | Ravizza . |
| 4,212,205 | 7/1980 | West et al. . |
| 4,277,758 | 7/1981 | Mishiro . |
| 4,389,891 | 6/1983 | Fournier . |
| 4,393,373 | 7/1983 | Torii et al. . |
| 4,399,514 | 8/1983 | Hamasaki et al. . |
| 4,406,157 | 9/1983 | Miyahara et al. . |
| 4,577,500 | 3/1986 | Mishiro . |
| 4,577,503 | 3/1986 | Imaino et al. . |
| 4,644,482 | 2/1987 | Juanarena . |
| 4,715,559 | 12/1987 | Fuller . |
| 4,783,987 | 11/1988 | Hager et al. . |
| 4,808,948 | 2/1989 | Patel et al. . |
| 4,849,668 | 7/1989 | Crawley et al. . |
| 4,869,097 | 9/1989 | Tittmann et al. . |
| 4,929,874 | 5/1990 | Mizuno et al. ............... 73/668 |
| 4,958,100 | 9/1990 | Crawley et al. . |
| 5,012,428 | 4/1991 | Ueno et al. ............... 73/663 |
| 5,060,974 | 10/1991 | Hamilton et al. . |
| 5,156,370 | 10/1992 | Silcox et al. ............... 73/579 |
| 5,195,046 | 3/1993 | Gerardi et al. . |
| 5,229,744 | 7/1993 | Ogura . |
| 5,233,274 | 8/1993 | Honda et al. . |
| 5,245,552 | 9/1993 | Anderson et al. . |

FOREIGN PATENT DOCUMENTS

| | | |
|---|---|---|
| 0247601 | 5/1987 | European Pat. Off. . |
| 0600491 | 12/1993 | European Pat. Off. . |
| 3428523 | 2/1985 | Germany . |
| 2272819 | 11/1993 | United Kingdom . |

*Primary Examiner*—George M. Dombroske
*Assistant Examiner*—William L. Oen
*Attorney, Agent, or Firm*—Michael S. Yatsko

[57] ABSTRACT

A self-exciting vibratory device for producing vibration signals in a housing includes actuator means (12) attached to housing (16), sensor means (14) attached to housing (16) and electronics module (18) connecting actuator means (12) and sensor means (14). Actuator means (12) creates vibration signals within housing (16). Sensor means (14) senses the vibration signals created by actuator means (12). Electronics module (18) amplifies and phase shifts the vibration signals sensed by sensor means (14) and containing resonant modes of vibration of housing (16). Electronics module (18) then supplies these amplified, phase shifted signals to actuator means (12) to enhance the vibration of housing (16) at the dominant mode of vibration of housing (16).

15 Claims, 3 Drawing Sheets

APPARATUS AND METHOD FOR PRODUCING STRUCTURAL AND ACOUSTIC VIBRATIONS

CROSS-REFERENCE TO RELATED APPLICATIONS

This is a continuation-in-part of U.S. patent application Ser. No. 986,035, filed Dec. 4, 1992 U.S. Pat. No. 5,351,527, in the name of Blackburn, et al., for "Method And Apparatus For Testing Fluid Pressure In A Sealed Vessel" and U.S. patent application Ser. No. 08/311,607, filed Sep. 23, 1994 in the name of Bronowicki et al., for "Method And Apparatus For Testing Fluid Pressure In A Sealed Vessel".

BACKGROUND OF THE INVENTION

1. Field of the Invention

This invention relates generally to resonators, and more particularly, to a device that both actuates and senses structural or acoustic vibrations within a housing.

2. Discussion

Many possible applications exist in which it is desirable to create a sustained resonance of a structural or acoustic mode of vibration. In one such application, in a personal paging device, it is desirable to create structural vibrations to produce a tactile alert, or radiated sound waves to produce an audible alert. In another application, it is desirable to generate sound waves from the resonance of a car or truck panel and use the sound waves as a horn for the car or truck. In, still other applications, it is desirable to generate a sustained resonance of a structural mode of vibration either in a resonant ring or inchworm motor for producing large relative translational or rotational motions through a series of small vibratory steps, or in an integral compressor in a refrigeration system by producing compression waves in an acoustic cavity through an induced vibration of a flexure mechanism.

In all of the above applications, the sustained resonance of either a structural or an acoustic mode of vibration within a structure can be achieved by driving a mechanism, such as an actuator, integrally attached to the structure to create the vibration. To create the vibration in an efficient manner, the actuator should be driven at a frequency coinciding with the natural resonance frequency of the target structural or acoustic mode of vibration. Driving the actuator at this natural frequency takes advantage of the natural dynamic amplification factor Q of the resonance by producing, from the given actuator input, a motion greater in amplitude than if the driving mechanism was driven in an off-resonant condition.

In the past, typical mechanically-tuned excitation devices have been used for various of the above applications. With such devices, a fixed sinusoidal signal, pretuned to coincide as closely as possible with the natural resonance frequency of the particular structure, is input into the structure. However, such mechanically-tuned devices are prone to errors due to manufacturing tolerances in the devices themselves. Further, these devices are limited in effectiveness due to various uncertainties such as temperature and humidity, which may affect stiffness and mass properties in the device. In addition, as the systems in which the vibratory devices are implemented change over time due to fatigue, creep and microcracking, the devices become less accurate. Also, the drive frequency of such devices often drifts due to the effect of varying temperatures on the electronic components of the devices. While many of these devices could be adjusted to compensate for the above conditions, typical vibratory devices have no means for automatically adjusting the excitation frequency to correspond to the target resonance frequency of the structures in which the devices are implemented.

In view of the above, what is needed then is a device that actuates structural or acoustic vibrations in real time, and senses these vibrations to insure that the excitation frequency coincides with the target resonance frequency at all times, thus maximizing efficiency in generating an induced vibration.

BRIEF DESCRIPTION OF THE DRAWINGS

The various advantages of the present invention will become apparent to those skilled in the art after a study of the following specification and by reference to the drawings in which.

SUMMARY OF THE INVENTION

In accordance with the teachings of the present invention, a self-exciting vibratory device is provided for generating structural or acoustic vibrations at a structure's natural resonance frequency within a desired pass band while simultaneously damping out of band modes of vibration. The self-exciting vibratory device finds particular utility in serving as an alert in a paging device or in serving as a horn in an automobile. The self-exciting vibratory device of the present invention also finds particular utility in serving as a test device for components manufactured on an assembly line, in functioning as an integral compressor for a refrigeration system, and in functioning as a small-scale fan for microelectronics cooling applications.

In the inventive approach, an apparatus is provided for producing vibration signals in a housing. The apparatus includes actuator means affixed to the housing for causing vibration signals. Further, sensor means are attached to the housing for sensing the vibrations created by the actuator means. Feedback means connects the actuator means and the sensor means and amplifies and phase shifts those vibration signals from the sensor means that contain resonant modes of vibration. The feedback means supplies these amplified, phase shifted signals to the actuator means, and, as a result, enhances the vibration of the housing at the natural resonance frequency of the structure or acoustic cavity. The excited modes of vibration may be either structural or acoustic vibrations, depending upon the desired application.

DETAILED DESCRIPTION

The following description of the preferred embodiments is merely exemplary in nature and is in no way intended to limit the invention or its application or uses.

Figure 1A:
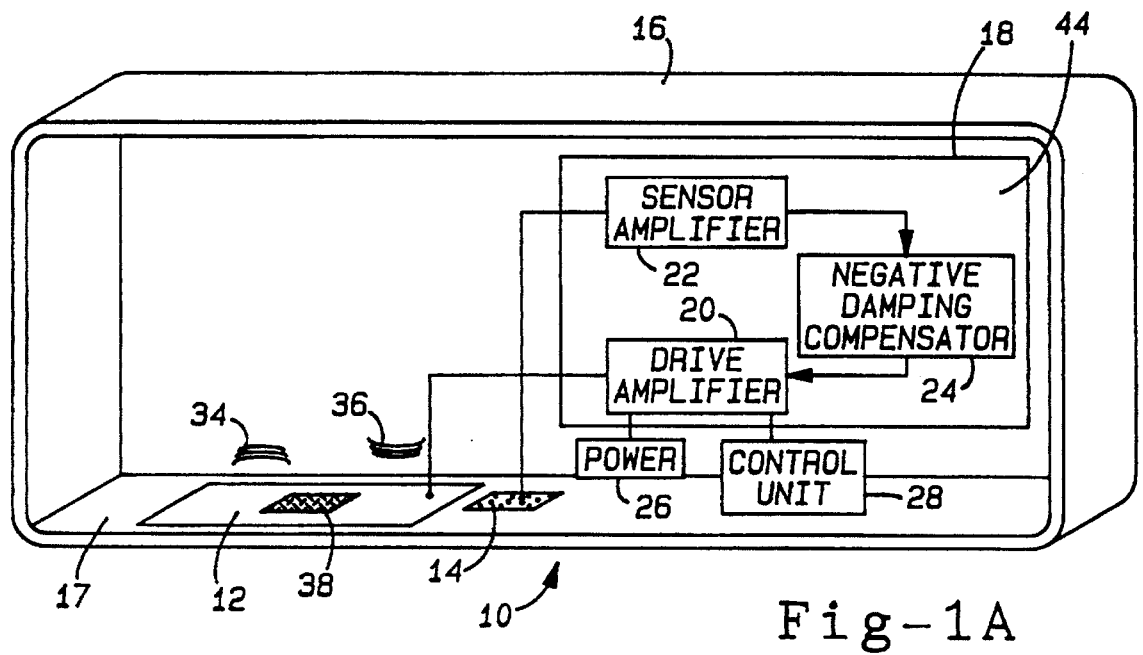
FIGS. 1A and 1B are perspective and side elevation views, respectively, showing a preferred embodiment of a self-exciting vibratory device of the present invention as implemented in a paging device.

Referring to the drawings, FIG. 1A illustrates a side elevation view of a self-exciting vibratory device, shown generally at 10. The device includes actuator 12 and sensor 14, which are both mounted inside a housing, such as the housing 16 of the paging device shown. Both actuator 12 and sensor 14 are preferably piezoelectric ceramic (PZT) transducers or piezoelectric polyvinylidenedifluoride (PVF$_2$) transducers. Actuator 12 and sensor 14 are thin and thus will conform to the shape of housing 16 to which the devices are affixed. Actuator 12 and sensor 14 are affixed to flexible base plate 17 of housing 16 through the use of an appropriate adhesive or clamp mechanism (not shown). Actuator 12 is used to generate vibrations within housing 16, and sensor 14 is used to detect the generated vibrations within housing 16, in a manner that will be described in more detail below. Actuator 12 and sensor 14 are preferably of the type disclosed in U.S. Pat. No. 986,035 to Blackburn et al. entitled "Method And Apparatus For Testing Fluid Pressure In A Sealed Vessel", filed Dec. 4, 1992, and U.S. patent application Ser. No. 08/311,607 to Bronowicki et al. entitled "Method And Apparatus For Testing Fluid Pressure In A Sealed Vessel", filed Sep. 23, 1994 which is a continuation-in-part of application Ser. No. 986,035. Both applications are hereby incorporated by reference.

Still referring to FIG. 1A, actuator 12 and sensor 14 are operatively connected to electronics module 18. Electronics module 18 consists of drive amplifier 20, sensor amplifier 22 and negative damping compensator 24.

Drive amplifier 20 provides an input voltage to actuator 12. Drive amplifier 20 is powered by power supply 26, which is a double-sided power supply or, in the case of the present invention being implemented in an automobile, power supply 26 may be a single-sided power supply with an artificial ground established so that the power supply functions as a double-sided power supply. Drive amplifier 20 and power supply 26 are in turn controlled by control unit 28. Control unit 28 may be any type of control unit capable of causing drive amplifier 20 to drive actuator 12 upon command.

Electronics module 18 further consists of sensor amplifier 22 connected to sensor 14 for converting vibration signals sensed by sensor 14 into corresponding voltage signals. Sensor amplifier may be an operational amplifier or any other type of amplifier well known to those skilled in the art.

Electronics module also includes negative damping compensator 24 for amplifying and phase shifting voltage signals received from sensor amplifier 22 that are within a predetermined passband, as will be described in more detail below. Negative damping compensator 24 then outputs the amplified, phase-shifted signals to drive amplifier 20. Drive amplifier 20 inputs these signals into actuator 12 to excite resonant mode vibrations within housing 16 and to damp off-resonant modes of vibration. Electronics module 18 thus functions as a positive feedback mechanism, allowing self-exciting vibratory device 10 to generate vibrations within housing 16 at the dominant mode of vibration of housing 16, while at the same time automatically adjusting for changes in temperature or pressure, and thus changes in the dominant mode of vibration, in housing 16. As with actuator 12 and sensor 14, electronics module 18 is disclosed in both aforementioned U.S. patent application Ser. Nos. 986,035 and 311,607.

Figure 2:
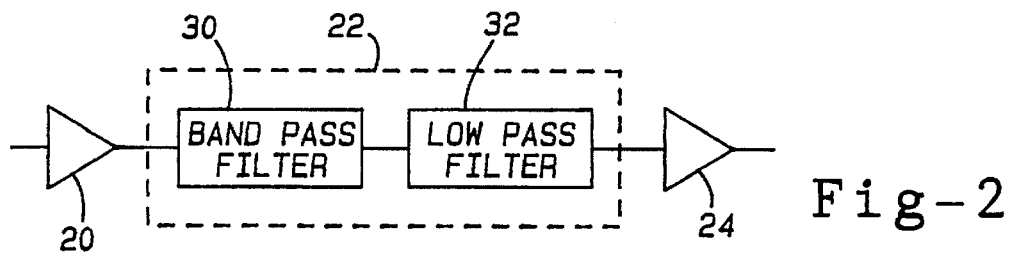
FIG. 2 is a block diagram showing the electronics module of FIG. 1 in more detail.

Referring to FIG. 2, negative damping compensator 22 of electronics module 18 is shown in more detail. Negative damping compensator 22 includes band pass filter 30 and low pass filter 32. The input of band pass filter 30 is connected to the output of sensor amplifier 20. The output of band pass filter 30 is connected to the input of low pass filter 32. The output of low pass filter 32 is connected to the input of drive amplifier 20. Band pass filter 30 is a two pole band pass filter of the type well known to those skilled in the art. Low pass filter 32 is a two pole low pass filter, also of the type well known to those skilled in the art. Alternately, the order of the two filters may be reversed.

Together, band pass filter 30 and low pass filter 32 operate to amplify and phase shift vibration signals transduced by sensor 14, and converted into voltage signals by sensor amplifier 20, thereby amplifying the natural resonance frequency, or dominant mode of vibration, of housing 16 and damping off resonant modes of vibration of housing 16 in manner that will be described in more detail below. Together, band pass filter 30 and low pass filter 32 amplify and phase shift signals from sensor 14 and sensor amplifier 22 in a fairly broad pass band known to contain resonant modes of vibration. Negative damping compensator 24 may be designed to pass selected harmonics and amplify the harmonics, while simultaneously providing a −90° phase shift for creating loop instability at the desired range of natural resonance frequencies.

Figure 1B:
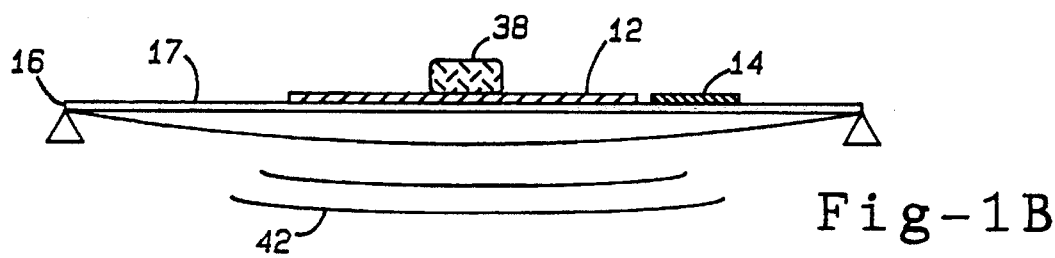

As shown in FIGS. 1A and 1B, mass 38 is secured to actuator 12 so that as drive amplifier 20 drives actuator 12, actuator 12 contracts and bends flexible base plate 17 of housing 16. As a result, mass 38 vibrates and causes an initial motion of the housing perceptible to humans. The paging device thus provides a vibratory, or tactile, alert capable of being felt by a person carrying such a pager device. Electronics module 18 also includes a switch 44 that allows one to switch the center frequency of the pass band of negative damping compensator 24 to switch between tactile and audible operation of the self-exciting vibratory device. In the audible mode a higher order resonance of a plate is excited, causing a sound wave, shown generally at 42 in FIG. 1B to be radiated.

Referring now to FIGS. 1A and 2, operation of the self-exciting vibratory device of the present invention will now be described. Upon receiving appropriate commands from control unit 28, drive amplifier 20, through power supply 26, drives actuator 12, thereby creating ambient, low-level vibration signals, shown generally at 34, within housing 16. As vibration signals 34 are reflected off of the walls of housing 16, as indicated generally at 36, sensor 14 senses the reflected vibration signals. Sensor amplifier 22 converts sensed vibration signals into corresponding voltage signals and supplies the voltage signals to negative damping compensator 24. Negative damping compensator 24 is designed to provide gain greater than 10 db at the natural resonance frequency of housing 16, thus causing the magnitude of the oscillation to grow. The magnitude of the oscillation is ultimately limited by the voltage supplied to drive amplifier 20 from power supply 26. Because the natural resonance frequency of housing 16 exhibits a −90° phase shift, negative damping compensator 24 is also designed to provide an additional −90° of phase shift to provide the necessary condition for loop instability of −180°. Signals falling within the passband and gain bandwidth of damping compensator 24 are amplified and phase shifted, while signals falling outside the passband and gain bandwidth are gain and phase stabilized.

Figure 3A:
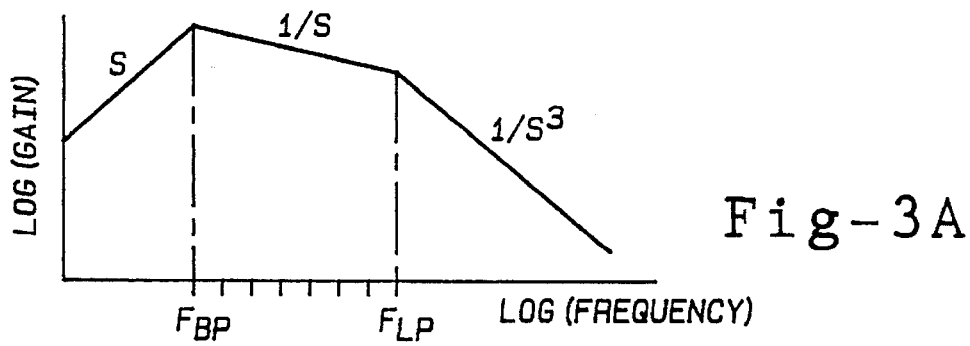
FIGS. 3A and 3B are graphical representations of the gain and phase responses, respectively, produced by the negative damping compensator of the present invention.
Figure 3B:
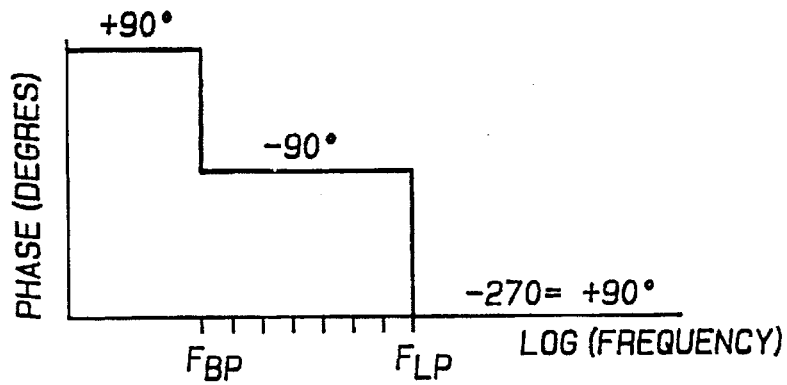

Referring to FIGS. 3A and 3B, in one embodiment, the frequency of the 2 pole bandpass filter is set below the range of desired oscillation frequencies. Below the natural frequency of the bandpass $f_{BP}$ filter a +90° phase shift is provided, stabilizing or damping these lower frequency vibrations. Above this frequency a −90° phase shift destabilizes resonances. The lowpass cutoff frequency $f_{LP}$ is placed above the range of desired oscillation frequencies, inducing a further −180° phase shift, for a total phase shift of −270° (+90°), again stabilizing the vibrations at higher frequencies. This design also gain stabilizes vibrations below the bandpass and above the lowpass cutoff frequencies, since the filters attenuate signals below and above those frequencies, respectively. The positive feedback from negative compensator 24 is then supplied to drive amplifier 20 as drive amplifier 20 drives actuator 12.

Figure 4:
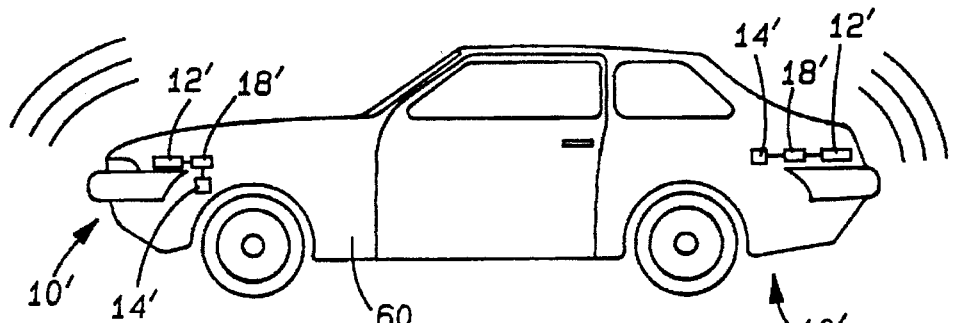
FIG. 4 is a side elevation view of a first alternate embodiment of the present invention used as a horn in an automobile.

FIG. 4 shows the self-exciting vibratory device of the present invention implemented as a horn in an automobile. Device 10' is identical to device 10, with the difference being that device 10' is mounted to the interior of automotive body panel 60 (the portions of body panel to which the device of the present invention is mounted are shown as being transparent in FIG. 4 for illustrative purposes only). Device 10' causes vibration of automotive body panel 60 at the body panel's natural resonance frequency, thereby creating in effect a directional horn for the automobile.

Figure 5:
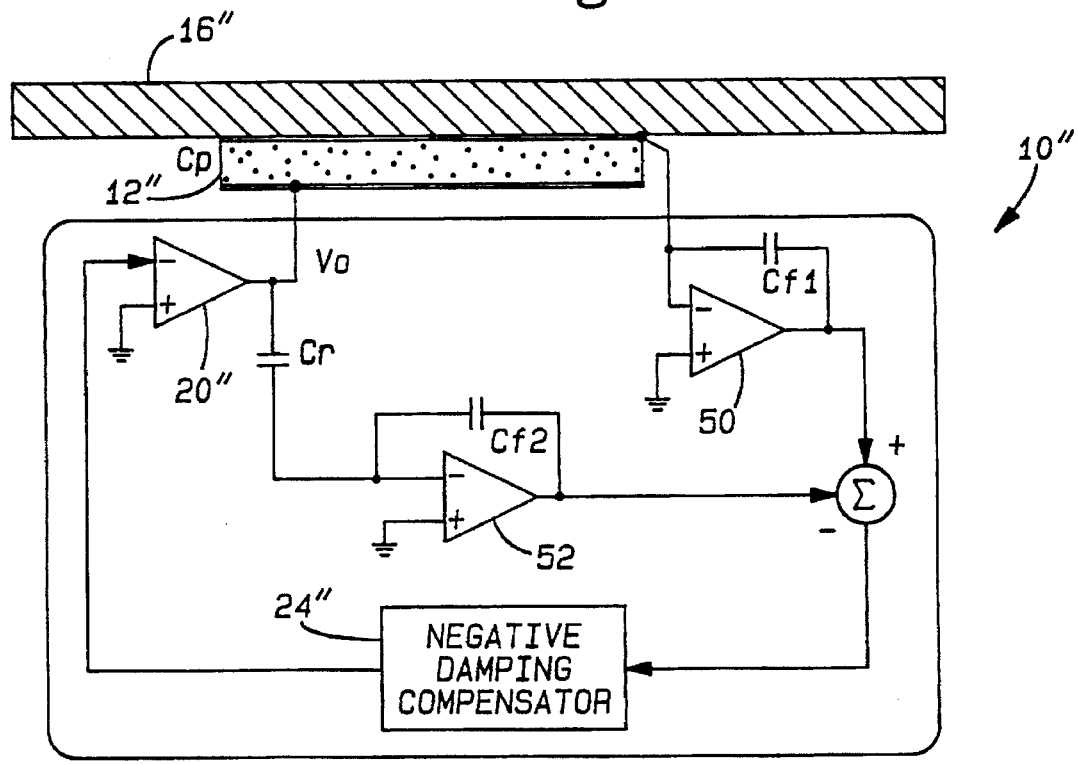
FIG. 5 is a side elevation view, partially in block diagram form and partially in schematic, of a second alternate embodiment of the present invention.

FIG. 5 shows an alternative embodiment of the self-exciting vibratory device of the present invention in which the actuator and the sensor components are combined into a single self-sensing actuator. Self-sensing actuator 12" is operatively connected to housing 16" in the same manner as actuator 12 and sensor 14 are attached to housing 16 in FIG. 1. Self-sensing actuator is composed of a piezoelectric material including an electrode on which a charge is deposited in response to the amplitude of vibration generated in housing 16" by the actuator 12". Self-sensing actuator 12" is described in an article by Anderson, Hagood and Goodliffe, entitled "Self-Sensing Piezoelectric Actuation: Analysis and Application to Controlled Structures", published in the 1992 AIAA SDM Conference Proceedings, and which is hereby incorporated by reference.

The electronics module 18" in which self-sensing actuator 12" is connected includes drive amplifier 20" and negative damping compensator 24", as in the electronics module 18 shown in FIG. 1. Electronics module 18" differs from electronics module 18 in that it includes charge amplifier 50 with corresponding capacitor $C_{F1}$ and charge amplifier 52 with corresponding capacitor $C_{F2}$, and reference capacitor $C_R$. Reference capacitor $C_R$ is connected along with charge amplifier 70 and capacitor $C_{F2}$ to self-sensing actuator 12" at the input $V_o$ of power amplifier 20". Charge amplifier 70 and capacitor $C_{F1}$ are connected to self-sensing actuator 12" at a second location. Charge amplifier 70 and capacitor $C_{F1}$ determine the charge deposited on self-sensing actuator 12", while reference capacitor $C_R$ and charge amplifier 72 provide a reference charge. The deposited charge and the reference charge are summed to produce a signal proportional to the strain on the self-sensing actuator 12". This signal is then input into negative damping compensator 24". Negative damping compensator 24" then phase shifts and amplifies the input signals proportional to the strain on self-sensing actuator 12", in a manner identical to that of negative damping compensator 24, to amplify signals at the natural resonance frequency of housing 16" and to negatively damp off-resonant modes of vibration. As the same compensator is applied to all modes, gain and phase shift are determined only by frequency of excitation.

Figure 6:
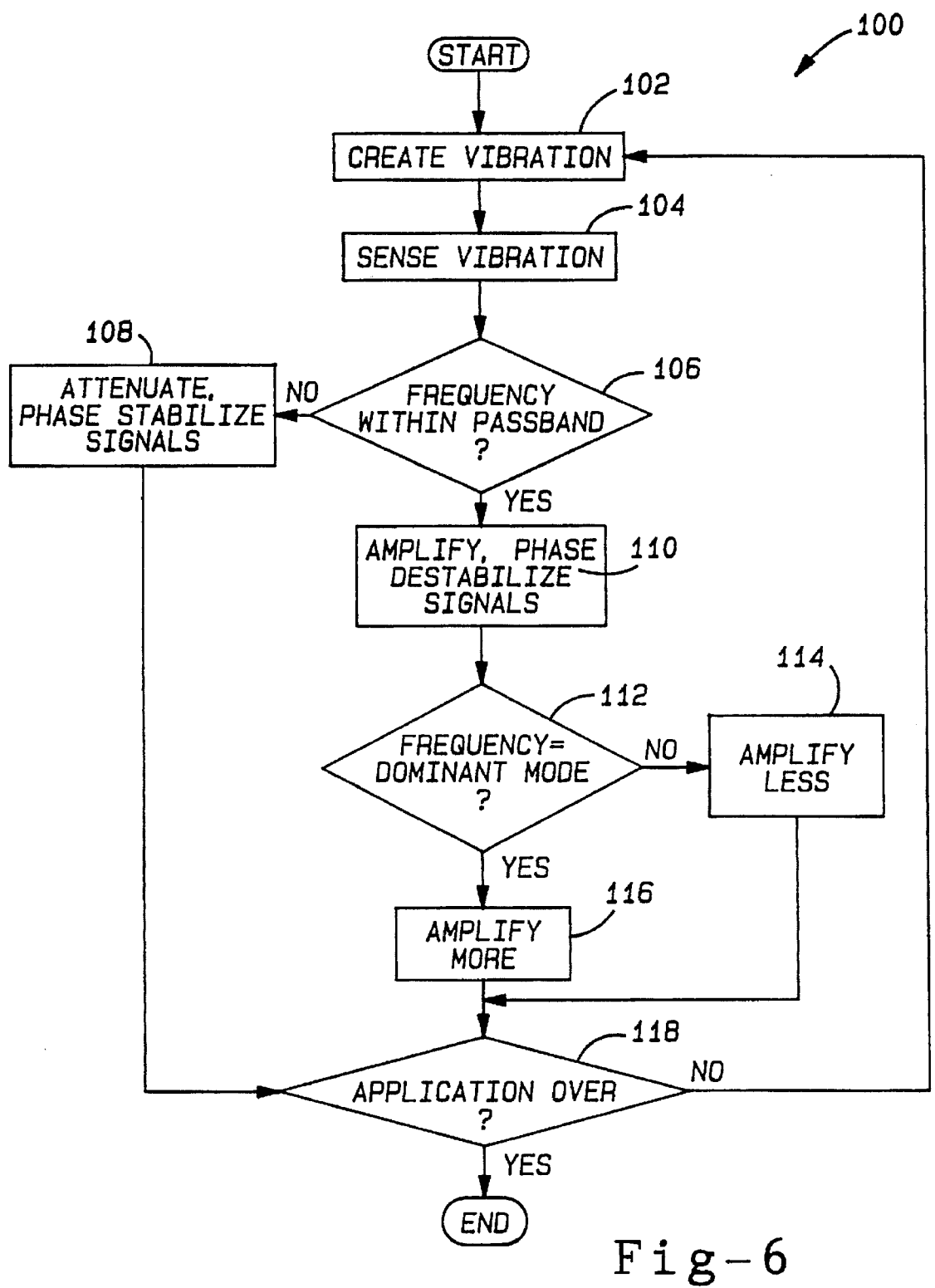
FIG. 6 is a flow diagram showing the method used for implementing the self-exciting vibratory device of the present invention.

FIG. 6 is a flow diagram, shown generally at 100, illustrating the operation of the self-exciting vibratory device of the present invention. At step 102, the device creates a vibration signal within the housing to which it is mounted. At step 104, the device senses generated vibration signals. At step 106, if vibration signals fall outside of the pass band of negative damping compensator 24, the vibration signals are attenuated and phase-stabilized, as indicated at step 108. If the vibration signals fall within the pass band at step 106, the signals are subsequently amplified and phase-shifted toward instability at step 110. At step 112, if the signals are not signals of the dominant acoustic or structural mode of vibration, the negative damping compensator 24 provides these signals to amplifier 20 which amplifies these modes of vibration to a lesser degree, as indicated at step 114. If the vibrations are at the dominant natural resonance frequency, negative damping compensator 24 amplifies the signals to a greater degree, and sends the amplified signals to drive amplifier 20 to increase the amplitude of the natural resonance mode within the housing, as indicated at step 116.

The amplitude of the natural resonance frequency continues to increase until it reaches a limit, usually due to the voltage supplied to drive amplifier 20 by power supply 26. Thus, housing 16 continues to resonate at either the dominant acoustic or structural mode of vibration. At step 118, if the particular application is over, drive amplifier 20 ceases to drive actuator 12. If the application is not over, drive amplifier 20 continues to drive actuator 12 until drive amplifier 20 receives a stop command from control unit 28.

As can be appreciated, the self-exciting vibratory device disclosed herein may be implemented in a wide variety of applications. The self-exciting vibratory device of the present invention may be used to create either structural or acoustic modes of vibration within a particular housing. The self-exciting vibratory device of the present invention allows a drive mechanism to cause a particular housing to resonate at its natural resonance frequency with minimum power input into the actuator itself. The self-exciting vibratory device of the present invention thus creates a sustained mode of resonance within the housing and, through a positive feedback loop, automatically adjusts for changes in the natural frequency in the housing due to fluctuations in temperature and pressure within the housing without the necessity of mechanically adjusting the device to compensate for the changes.

Various other advantages of the present invention will become apparent to those skilled in the art after having the benefit of studying the foregoing text and drawings, taken in conjunction with the following claims.

What is claimed is:

1. An apparatus for producing vibration signals in a housing comprising:

actuator means attached to said housing for creating said vibration signals;

sensor means attached to said housing for sensing said vibration signals created by said actuator means; and feedback means connecting said actuator means and said sensor means for amplifying and phase shifting said vibration signals from said sensor means containing resonant modes of vibration of said housing, said feedback means supplying said amplified, phase shifted signals to said actuator means for enhancing vibration of said housing at said natural resonance frequency of said housing.

2. The apparatus of claim 1, wherein said feedback means comprises:

a sensor amplifier connected to said sensor means for amplifying said vibration signals sensed at said sensor means;

a negative damping compensator for phase shifting said amplified vibration signals from said sensor amplifier to produce negative damping signals;

a drive amplifier for driving said actuator means and for providing said negative damping signals to said actuator;

said feedback means producing oscillation of said housing, said feedback means capable of changing frequency to track said natural resonance frequency of said housing as said natural resonance frequency of said housing changes due to pressure or temperature variations in said housing.

3. The apparatus of claim 1, wherein said actuator means comprises a piezoelectric ceramic transducer.

4. The apparatus of claim 1, wherein said sensor means comprises a piezoelectric ceramic transducer.

5. The apparatus of claim 1, wherein said sensor means comprises a polyvinylidenedifluoride film.

6. The apparatus of claim 1, wherein said actuator means comprises a polyvinylidenedifluoride film.

7. The apparatus of claim 1, wherein said natural resonance frequency of said housing is an acoustic frequency.

8. The apparatus of claim 1, wherein said natural resonance frequency of said housing is a structural frequency.

9. The apparatus of claim 1, wherein said actuator means and said sensing means are located in a actuator.

10. The apparatus of claim 1, wherein said feedback means provides a −90° phase shift to said vibration signals to produce said negative damping signals.

11. The apparatus of claim 1, wherein said actuator means is affixed in a first location to a flexible base plate of said housing.

12. The apparatus of claim 10, wherein said sensor means is affixed in a second location to said flexible base plate of said housing.

13. The apparatus of claim 11, wherein said feedback means is mounted within said housing.

14. A system, comprising:

a housing;

an actuator attached to said housing for flexing portions of said housing and for creating vibration signals within said housing;

a sensor attached to said housing for sensing said vibration signals created by said actuator within said housing;

an electronics module connected to said actuator and said sensor, including:

a sensor amplifier for converting said vibration signals sensed by said sensor into voltage signals;

a negative damping compensator for phase shifting and amplifying said voltage signals from said sensor amplifier in a pass band known to contain resonant modes of vibration of said housing; and a drive amplifier for driving said actuator and for supplying said amplified, phase shifted signals in said pass band to said actuator to cause said housing to resonate at a natural resonance frequency of said housing;

said phase shifted signals from said pass band enhancing vibration of said housing at said natural resonance frequency;

said system capable of adapting to changes in said natural resonance frequency of said housing, due to fluctuations in stiffness and mass properties within said housing, to sustain vibration of said housing at said natural resonance frequency.

15. A method for creating a sustained resonant mode of vibration comprising the steps of:

providing a housing;

generating vibration signals within said housing;

detecting said vibration signals;

amplifying said vibration signals;

phase shifting said vibration signals in a pass band containing resonant modes of vibration of said housing;

supplying said amplified, phase shifted signals to said actuator to increase said vibration signals at said natural resonance frequency of said housing in amplitude; and changing said amplified, phase-shifted signals supplied to said actuator to track said natural resonance frequency of said housing as said natural resonance frequency changes due to variations in stiffness and mass properties within said housing.

* * * * *